United States Patent [19]
Kröger et al.

[11] Patent Number: 6,008,038
[45] Date of Patent: Dec. 28, 1999

[54] METHOD AND A CIRCUIT ARRANGEMENT FOR THE ELECTROPERMEATION OF LIVING CELLS

[75] Inventors: Wolfgang Kröger, Gudow; Bernd Jagdhuber, Uetersen; Hans-Joachim Ricklefs, Hamburg, all of Germany

[73] Assignee: Eppendorf-Netheler-Hinz GmbH, Hamburg, Germany

[21] Appl. No.: 09/044,210

[22] Filed: Mar. 18, 1998

[51] Int. Cl.[6] .................................................. C12M 3/00
[52] U.S. Cl. .................................. 435/285.2; 435/286.1; 227/542; 361/232
[58] Field of Search .............................. 435/285.2, 286.1, 435/173.6; 227/538, 542; 361/232

[56] References Cited

U.S. PATENT DOCUMENTS

| | | | |
|---|---|---|---|
| 5,273,525 | 12/1993 | Hofmann | 604/21 |
| 5,439,440 | 8/1995 | Hofmann | 604/20 |

FOREIGN PATENT DOCUMENTS

| | | | |
|---|---|---|---|
| 3718941 | 2/1988 | Germany | A61N 1/00 |
| 2227380 | 4/1991 | United Kingdom | C12N 13/00 |

*Primary Examiner*—David A. Redding
*Attorney, Agent, or Firm*—Brown & Wood, LLP

[57] ABSTRACT

A method for the electropermeation of living cells between at least two electrodes over a predetermined interval with an electrical potential or a current, characterised by the following features:

- a voltage or current source which is not exhaustable over the interval is applied to the electrodes via a controllable power semiconductor functioning as a regulator;
- the course of the potential or of the current during the interval is predetermined by a setting value transducer which generates any selectable course of curve, and is inputted to a controller which is connected in front of the driver step for the power semiconductor;
- the controller receives a value, as an instantaneous value, corresponding to the actual potential or current applied at the electrodes;
- the interval has a time range of a few 100 ns to several minutes.

4 Claims, 1 Drawing Sheet

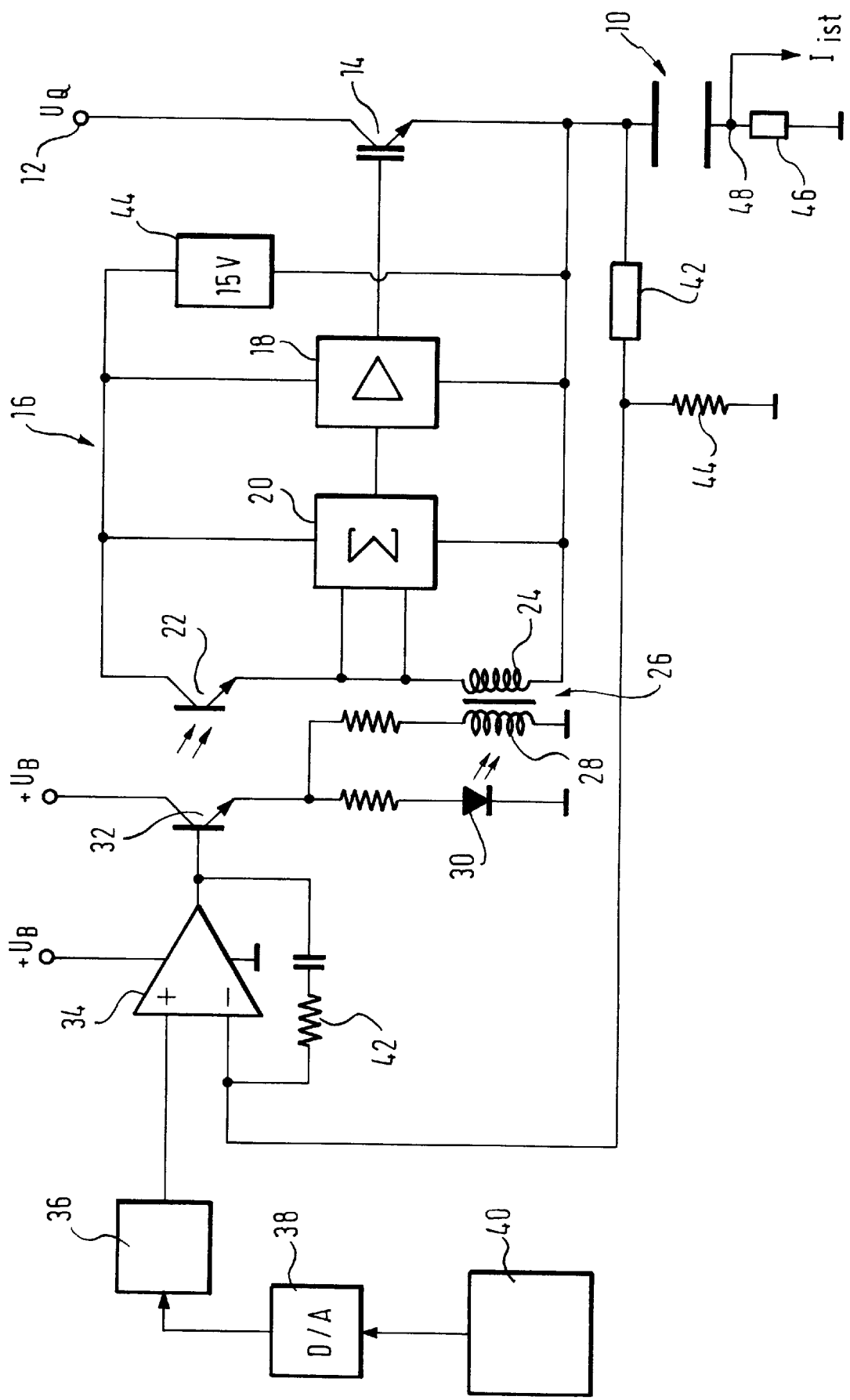

METHOD AND A CIRCUIT ARRANGEMENT FOR THE ELECTROPERMEATION OF LIVING CELLS

The invention relates to a method for electropermeation of living cells according to the preamble of patent claim 1.

It is known for the purpose of detection, expression, marking, structural clarification, enriching, separation, aptosis, gene regulation, gene therapy, transformation, cell to cell interaction, etc. to introduce molecules and particles into living cells. For this it is necessary to make the cell membrane temporarily permeable without the inside of the cell and the survival capacity of the cells being noticeably compromised. The current method of choice is lipofection. Another possible method is electroporation or electropermeation. With this method the living cells are brought into an electrical field of a relatively high field strength but over a relatively short duration. With a correct choice of parameters it is possibele to incorporate one micro-opening into the cell membrane which is expanded to a certain measure by electrophoresis. Via this opening it is then possible to inwardly transfer molecules or particles into the cell. As molecules, e.g. nucleic acids, proteins, enzymes, regulator proteins, ligands, receptors, antibodies, contrast means for X-rays, for NMR and for ultrasound examinations and electron microscopy are to be considered. Particles may e.g. be chromosomes, viruses, organelles or cells, magnetic particles, gold, carbon, etc.

The described electroporation takes place in vitro as well as also in vivo. With in-vitro electroporation the living cells are located in a suspension of a suitable fluid, which is brought into a sample vessel (cuvette). The sample vessel is provided with electrode plates (plate capacitor). With the in-vivo electroporation electrodes, for example in the form of needles, are introduced into body regions. The present invention generally relates to electroporation.

From GB 2 227 380 or DE 37 18 941 it is known to apply to the electrodes of a sample vessel a voltage in the form of a rectangular impulse of a predetermined duration and height. The current is larger than 100 amps and the voltage is about 3000 volts. As a voltage source there serves a capacitor which is switched via a power switch onto the electrodes of the sample vessel. As a power switch there serves a number of thyristors arranged in parallel. The switching time of the thyristors is monitored. When the predetermined time has been reached the thyristors are blocked.

From U.S. Pat. No. 5,273,525 or U.S. Pat. No. 5,439,440 an in vivo electroporation is known with which variously shaped pulses are applied to the electrodes, for example pulses with exponentially decaying flanks, rectangular pulses, unipolar or bipolar oscillating pulses which between the electrodes produce a field strength of 0.2 kV/cm to 20 kV/cm. The pulse length is between 10 and 100 ms, wherein up to 100 pulses may be produced after one another. In these documents it is also mentioned that the parameters of the electroporation are to be selected according to which conditions are to be met, i.e. how the cells are natured. The field strength and the duration of the pulses must consequently be varied in order on the one hand to achieve the desired parameters and on the other hand to avoid damaging the cells.

It has however been ascertained that it is not sufficient to input the course of the voltage or the current to the electrodes of the sample container in that a generator is controlled in a suitable manner, since the actual conditions with respect to the applied fluid and the type and nature of the living cells have other field strengths in its wake than should occur by way of the voltage input and geometry of the electrodes. The field strength which sets in in each case is as known dependent on the relative permittivities of the various media in the sample vessel, as well as on the current-conducting ability of the media whose properties mostly cannot exactly be reproducably induced.

It is therefore the object of the invention to provide a method for the electropermeation of living cells, which functions effectively but at the same time improves the survival rate of the cells in a lasting manner.

This object is achieved by the features of patent claim 1.

With the method according to the invention the course of the potential or of the current is set via the electrodes of the sample vessels. The optimal parameters for the course or the duration of the interval are determined empirically. In one formation of the invention the interval lies between 15 and 500 $\mu$s, which is relatively short compared to other methods. With the method according to the invention further the course of the voltage or of the current is monitored and is supplied by way of an instantaneous value transducer to a controller which delivers the signals for the control of a power semiconductor via which a voltage source is connected to the electrodes. With the method according to the invention consequently the power semiconductor is not applied as a switch but as a servo component or control member for regulating the voltage to be applied to the electrodes over the instructed time interval.

If with suitable experiments it results that a certain shape of voltage course with an effective electroporation ensures a high survival rate with a high number of permeated cells then the method according to the invention is in the position to make ready the corresponding electrical field strength.

A circuit arrangement for the electropermeation of living cells envisages an electronic control circuit which produces regulating signals for the driver stage of a controllable semiconductor. According to one formation of the invention this is an Insulated Gate Bipolar Transistor (IGBT) as is known per se from power electronics, in particular from power converters. An instantaneous value transducer acquires the current or the voltage at the electrodes and delivers a corresponding instantaneous value to the electronic control circuit. From the setting value transducer which may produce any course of curve, the course shape of the voltage or of the current over a predetermined interval is inputted.

The voltage or current source may be formed by a capacitor as is known per se from the state of the art. For the invention it is however essential than the capacitance of the capacitor is dimensioned adequately large so that with respect to the time interval the capacitor serves as a non-exhaustable source. The shape of the pulse to be applied to the electrodes is determined alone by the setting value transducer. This can according to a further formation of the invention be formed by a computer whose continuous output signal is given to the electronic control circuit via a digital-analog converter. With the help of a stepped course of the output signal of the computer any curve may be produced in that the stepped signal is converted into an analog signal. Thus for example the pulse may comprise an exponentially decaying course as is basically also known per se. The length of the steps of the output signal is directed as to how an approximation to the desired course of the curve can be most favourably achieved.

It is further known per se to galvanically separate the control electronics from the driver stage for a semiconductor regulator. For this purpose a transformer or an optocoupler may be applied. According to one formation of the invention the coupling of the control switch to the driver stage provides for a parallel connection of the optocoupler and the transformer, wherein the output signals of these elements are summed in a summing step. With the help of both coupling elements the fact is used that pulses of a desired length with extremely steeply rising flanks are transmitted which is beneficial to the speed of the control.

The invention is hereinafter explained in more detail by way of one embodiment example.

The single FIGURE shows a circuit for the electropermeation of living cells according to the invention.

In the drawing, 10 designates the electrodes on a sample vessel which form a type of plate capacitor with a predetermined distance. The electrodes 10 are applied to a terminal voltage $U_Q$ produced on a binding post 12, this being via an IGTB 14. The voltage source may e.g. be a capacitor of a relatively large capacitance (not shown) which can be applied to the binding post 12 via a switch which is not shown.

A driver stage 16 for the IGTB comprises an amplifier 18 whose input is connected to a summing stage 20 whose inputs are connected on the one hand to the emitter of a light-sensitive transistor 22 and on the other hand to the secondary coil 28 of a transformer 26. The primary coil 28 of the transformer 26 lies parallel to a light-emitting diode 30 which with the transistor 22 forms an optocoupler, The diode 30 and primary coil 28 are connected to the emitter of a transistor whose collector lies at the operating voltage $U_B$. The base of the transistor 32 is connected to the output of an operational amplifier 34. The positive input of the operational amplifier 34 is connected to a setting value transducer 36 which is connected to a computer 40 via a digital-analog converter 38. The negative input of the operational amplifier 34 is connected to a point between the IGTB 14 and the electrodes 10 via a resistance 42. The resistance 42 with a resistance 44 lying in parallel to the electrodes 10 forms a voltage divider. Between the electrodes 10 and earth there is connected a shunt 46 for the purpose of acquiring the current flowing over the elecrodes 10.

It is assumed that the electrodes 10 are supplied with a voltage which is applied in an interval of 15 to 100 μs and has an exponentially decaying course. For this purpose the switch which connects to voltage source which is not shown to the binding post 12 must be closed. This may be controlled via the computer 40. At the same time the computer 40 produces the nominal function by inputting a curve whose course is step-like in a manner such that it is approximated largely to the desired curve when it is converted into an analog signal via the digital-analog converter 38. Via the analog setting value transducer 36 this signal is inputted to the operational amplifier 34, this produces with the help of the transistor 32 and the described coupling to the driver stage 16 a regulating signal for the driver stage 16 which so triggers the IGTB in accordance with the setting signal that the voltage decaying at the electrodes 10 has the desired course and size. Since this is not automatically the case as has been previously mentioned, the voltage is fed back to the input of the operational amplifier 34 via the voltage divider 42, 44, in order to effect a control.

It is still to be mentioned that the amplification factor is set by the feedback loop 42. The IGBT 14 may be comprised of a multitude of IGBTs connected in parallel. The step 44 provides for a voltage offset.

In order to prevent damaging it is useful to monitor the current, which is the case with tapping with a current meter at 48. If the current exceeds a predetermined measure, the voltage source is disconnected.

It is also conceivable instead of the described voltage control, to effect a current control. For this purpose then the current instantaneous value is inputted to the electronic control which principally is constructed similarly as for the voltage control.

We claim:

1. A circuit arrangement for the electropermeation of living cells with a voltage or current source, which during a predetermined interval can be connected via a controllable semiconductor to electrodes and with a device for triggering the controllable semiconductor, wherein the voltage or current source is connected, via the controllable semiconductor (14) functioning as regulating element, to the electrodes (10), the regulating signals for the driver step (16) of the controllable semiconductor (14) are produced by an electronic control circuit, to which there is connected a setting value transducer which predetermines the course of the potential or of the current, as well as an instantaneous value transducer acquiring the potential or the current at the electrodes (10), and the output of the electronic control circuit is coupled to the driver stage (16) via potential separating stage (22, 30; 26).

2. A circuit arrangement according to claim 1, wherein the controllable semiconductor (14) is an IGBT.

3. A circuit arrangement according to claim 1 or 2, wherein the setting value transducer comprises a computer (40) whose step-shaped output signal is inputted to the control circuit via a digital-analog converter (38).

4. A circuit arrangement according to claim 1, wherein the coupling of the control circuit to the driver stage (16) is effected in parallel via an optocoupler (30, 22), and a transformer (26), and the circuit arrangement further comprises a summing stage (20) in which output signals from the optocoupler and the transformer are summed in a summing step.

* * * * *